United States Patent [19]

Shimizu et al.

[11] Patent Number: 4,709,089

[45] Date of Patent: Nov. 24, 1987

[54] METHOD FOR REFINING 2-(ARYL SUBSTITUTED) PROPIONIC ACID OR ITS SALT

[75] Inventors: Isoo Shimizu; Yasuo Matsumura, both of Yokohama; Yoshihisa Inomata, Kawasaki, all of Japan

[73] Assignee: Nippon Petrochemicals Company, Limited, Japan

[21] Appl. No.: 11,734

[22] Filed: Feb. 6, 1987

[30] Foreign Application Priority Data

Feb. 8, 1986 [JP] Japan ................................. 61-26246
Feb. 8, 1986 [JP] Japan ................................. 61-26248

[51] Int. Cl.$^4$ ............................................ C07C 51/42
[52] U.S. Cl. ................................... 562/494; 562/460; 562/465; 562/466
[58] Field of Search ................ 562/494, 460, 465, 466

[56] References Cited

U.S. PATENT DOCUMENTS 1,919,023 7/1932 Jaeger .................................. 562/494

FOREIGN PATENT DOCUMENTS 12780 8/1965 Japan .................................. 562/494

*Primary Examiner*—Paul J. Killos
*Attorney, Agent, or Firm*—Scully, Scott, Murphy & Presser

[57] ABSTRACT

An effective method for refining 2-(aryl substituted)-propionic acid or its salt which is characterized in that 2-(aryl substituted)propionic acid or its salt containing halogenated by-products is brought into contact with hydrogen in a liquid phase containing water under a basic condition at temperatures in the range of 20° C. to 170° C. in the presence of a catalyst of transition metal of the group VIII in the periodic table, thereby dehalogenating said halogenated by-product and producing highly pure 2-(aryl substituted)propionic acid or its salt.

8 Claims, No Drawings

METHOD FOR REFINING 2-(ARYL SUBSTITUTED) PROPIONIC ACID OR ITS SALT

BACKGROUND OF THE INVENTION (1) Field of the Invention

This invention relates to a method for refining 2-(aryl substituted)propionic acid or its salt (hereinafter referred to simply as "substituted propionic acid" which is useful as a medicine or an intermediate for preparing organic chemicals such as medicines. More particularly, the present invention relates to a method for refining to prepare highly pure 2-(aryl substituted)propionic acid in which the refining is attained by hydrogen treatment of halogenated by-products such as the halide of substituted propionic acid that are produced together with substituted propionic acid in the procedure of synthesis.

The present invention can be applied, for example, to the preparation of 2-(p-isobutylphenyl)propionic acid or its salts (hereinafter referred to as "IPA") which is used as a medicine or an intermediate for preparing organic chemicals such as medicines. More particularly, the invention relates to a method for recovering highly pure IPA from the remained filtrate of recrystallization, in which method the refining is carried out by hydrogen treatment of halogenated by-products such as halide of IPA (hereinafter referred to as "halogenated IPA") that remains together with IPA in the filtrate of recrystallization.

(2) Description of the Prior Art

In connection with the method for preparing 2-(aryl substituted)propionic acid, various methods have been hitherto proposed. For example, with regard to 2-(p-isobutylphenyl)propionic acid, there are proposed several methods using a starting material of isobutylacetophenone that is prepared by acetylating isobutylbenzene with acetyl chloride in the presence of aluminum chloride catalyst.

(a) A method utilizing Darzens' reaction causing isobutylacetophenone to react with α-chloroacetic acid in the presence of a salt of alkali metal hydroxide to form epoxy compound, is disclosed in British Patent No. 1,521,906.

(b) Methods utilizing methylation by reacting it with chloroform in the presence of a phase transfer catalyst such as a tert-ammonium salt, are disclosed in British Patent Nos. 971,700 and 2,055,814.

Furthermore, there are methods which start directly from isobutylbenzene.

(a) A method utilizing the reaction with an acyl halide in the presence of aluminum chloride catalyst is disclosed in British Patent No. 971,700.

(b) Methods utilizing chloromethylation with formaldehyde in the presence of hydrochloric acid, or utilizing Grignard reaction to halogenated isobutylbenzene that is obtained by direct halogenation are disclosed in U.S. Pat. Nos. 3,959,364 and 4,433,160 and British Patent No. 2,065,656.

(c) Methods utilizing alkylation reaction in which a halide is reacted in the presence of a metal chloride catalyst such as aluminum chloride are disclosed in U.S. Pat. No. 4,031,215 and Canadian Patent No. 1,077,960.

Furthermore, with regard to 2-(m-benzoylphenyl)-propionic acid, a preparation method is disclosed in Japanese Laid-Open Patent Publication No. 55-4311. Still further, another method for preparing 2-(aryl substituted)propionic acid is disclosed in U.S. Pat. No. 4,329,507.

However, in these conventional methods in which several procedures are combined, halogenated compounds which are liable to cause side reaction, are used as raw materials in synthesizing step, or halogenated compounds such as aluminum chloride are used as catalysts. In these reactions, dehalogenation is liable to occur during reaction and reaction agents have a tendency to release free halogen molecules or halogen ions. Thus, various side reaction occurs by the free halogen molecules or halogen ions, which leads the halogenation of starting materials, intermediates during synthesizing process and aimed reaction products. Even though the quantities of halogen compounds are small, the generation of halogenated by-product which is undesirable for the use of the aimed product cannot be avoided. Furthermore, the contamination with halogenated by-product, even when the quantity is very small, is not desirable for the substituted propionic acid which is used in the fields such as medicine in which high purity and high safety are required.

In the refining operation to eliminate impurities, recrystallization is generally adopted, because it cannot generally be attained by distillation. When the contamination with impurities like halogenated by-products must be severely avoided by recrystallization, relatively large quantity of substituted propionic acid is caused to remain in filtrate, which fact inevitably reduces the yield of crystalline substituted propionic acid. Furthermore, in order to eliminate halogenated by-products severely, intricate treatment such as increased number of repetition of recrystallization is also required.

It is difficult to define the chemical structures of the halogenated by-products contained in the 2-(aryl substituted)propionic acid because its quantity is quite small and, for example, as to beforesaid halogenated IPA, there are many isomers of halogenated IPA. Accordingly, the refining of 2-(aryl substituted)propionic acid by chemical method has never been proposed yet.

BRIEF SUMMARY OF THE INVENTION

The inventors have found that dehalogenation of halogenated by-product can be easily attained by hydrogen treatment in the presence of a transition metal catalyst in the presence of liquid phase water under basic condition, thereby accomplishing the present invention.

It is, therefore, the primary object of the present invention to provide an improved method for recovering highly pure, that is, halogen free 2-(aryl substituted)propionic acid.

Another object of the present invention is to provide a method for effectively recovering highly pure 2-(aryl substituted)propionic acid or its salt such as 2-(p-isobutylphenyl)propionic acid or its salts from the filtrate of recrystallization process.

The present invention, accordingly, proposes a refining method for producing highly pure 2-(aryl substituted)propionic acid or its salt which is characterized in that 2-(aryl substituted)propionic acid or its salt containing halogenated by-products is brought into contact with hydrogen in a liquid phase in the presence of a catalyst of transition metal of the group VIII in the periodic table and liquid phase water under basic condition, thereby dehalogenating the halogenated by-product and giving highly pure 2-(aryl substituted)propionic acid or its salt.

Furthermore, the present invention also proposes a method for recovering highly pure 2-(aryl substituted)-propionic acid or its salt which is characterized in that, in the refining process for 2-(aryl substituted)propionic acid or its salt by recrystallization, the 2-(aryl substituted)propionic acid, its salts and their halides contained in the filtrate of recrystallization are brought into contact with hydrogen in a liquid phase in the presence of a catalyst of transition metal of the group VIII in the periodic table and in the presence of water, thereby dehalogenating the halides and giving highly pure 2-(aryl substituted)propionic acid or its salt.

According to the present invention, it is possible to obtain highly pure substituted propionic acid containing substantially no halogenated by-product. For this reason, in the fields such as the field of medicines in which special refining is required, the operation of recrystallization can be made easy and the efficiency in recovering crystals can be much raised. In addition to the above advantage, the halogenated by-products are converted into the aimed substituted propionic acid by hydrogen treatment. Therefore, the side effect that the components generally regarded as impurities can be recovered as the aimed compound, is obtained.

Furthermore, according to the method of the present invention, highly pure 2-(aryl substituted)propionic acid such as IPA containing substantially no halogenated by-product such as halogenated IPA can be recovered from the filtrated containing 2-(aryl substituted)propionic acid such as IPA in recrystallization process, which filtrate is otherwise regarded as to be discarded. Therefore, in the fields in which special refining is required such as in the field of medicines, even when the recovery rate in each recrystallization step is made low, the overall recovery rate can be raised by adoption of the present invention. In addition as described above, the halogenated by-product such as halogenated IPA is converted into the aimed 2-(aryl substituted)propionic acid such as IPA itself by hydrogen treatment. Therefore, the side effect that the components generally regarded as impurities can be recovered as the aimed compound, can also be expected.

DETAILED DESCRIPTION OF INVENTION

The 2-(aryl substituted)propionic acid obtained by the method of the present invention is the one having 8 to 18 carbon atoms and an aryl substituent group on the carbon atom at the second position of the carboxylic acid.

In the case of (aryl substituted)propionic acid having 19 or more carbon atoms, it is not desirable in that the efficiency of dehalogenation is worse even under a basic condition, owing to the lack of solubility to water.

The aryl substituent groups are exemplified by a phenyl group, lower alkyl-substituted phenyl groups such as methylphenyl group, ethylphenyl group, dimethylphenyl group, propylphenyl group and butylphenyl group; alkoxy-substituted phenyl groups having an oxygen atom such as methoxy phenyl group, ethoxy phenyl group, propoxy phenyl group and butoxy phenyl group; and other substituted phenyl groups such as alkylphenoxyphenyl group and alkylbenzyl group, as well as substituted naphthyl groups such as methylnaphthyl group and methoxynaphthyl group. If any one of these aryl substituent groups is introduced into second position of the carboxylic acid, it is desirable because the marked advantage of the present invention can be expected owing to the fact that the hydrogen atoms bonded to the carbon atom in a second position are active and are liable to suffer halogenation in synthesis process.

The 2-(aryl substituted)propionic acids are exemplified by 2-phenylpropionic acid, 2-(p-alkylphenyl)propionic acids such as 2-(p-isobutylphenyl)propionic acid, 2-(aryloxyphenyl)propionic acid such as 2-(m-phenoxyphenyl)propionic acid, 2-(arylcarbonylphenyl)propionic acid such as 2-(m-benzoylphenyl)propionic acid, and 2-(methoxynaphthyl)propionic acid such as 2-(6-methoxynaphthyl)propionic acid.

The method of the present invention can be applied to any of substituted propionic acid or its salt if it contains halogenated by-products, that is synthesized by any conventionally known method.

Furthermore, as the substituted propionic acid containing halogenated by-products, it may be any of the product isolated in synthesizing process, the remaining filtrate in recrystallization process containing condensed halogenated by-products, or else.

In the recrystallization, the filtrate as a remainder solution after filtering off a precipitate of aimed product, naturally contains much impurities even though it also contains the aimed product to some extent. Accordingly, the filtrate is generally discarded as it stands. However, it is quite desirable that, when the method of the present invention is applied to such the filtrate, highly pure 2-(aryl substituted)propionic acid can be recovered from the hitherto discarded filtrate. In this case, the filtrate itself can be used as a starting material for the method of the present invention and the solid material that is obtained by evaporating the solvent of the filtrate can also be used as the starting material.

In the above recrystallization which utilizes the difference in dissolving power with the change of temperature, the conventionally known solvents of alcohols such as methanol and ethanol, and lower paraffins such as hexane and heptane can be used singly or in combination of two or more kinds. When the solvent is water miscible one such as alcohol, it can be used by mixing with water in order to adjust the dissolving power to 2-(aryl substituted)propionic acid such as IPA.

The dehalogenation, i.e., hydrogen treatment in the method of the present invention is carried out in a liquid phase. That is, 2-(aryl substituted)propionic acid or its salt is dissolved in a suitable organic solvent or water.

As an organic solvent, any suitable one of the foregoing solvents for recrystallization and other appropriate ones can be used as far as it does not hinder the hydrogen treatment and it can dissolve the 2-(aryl substituted)propionic acid or its salt. In view of the removal of the solvent from the reaction system after the hydrogen treatment, the low boiling point of the solvent is desirable. The organic solvents are typically exemplified by paraffins such as n-hexane and n-heptane; cycloparaffins such as cyclohexane; alcohols such as methanol, ethanol and ethylene glycol; and ethers such as acetone, dioxane and tetrahydrofuran. These organic solvents and water can be used as a mixture of two or more kinds.

When a salt of 2-(aryl substituted)propionic acid is refined, water is necessary to dissolve it. In this case, other organic solvent can exist together with water.

The catalyst used in the hydrogen treatment of the present invention is any of metals of the group VIII in the periodic table. Among them, platinum (Pt), rhodium (Rh) and palladium (Pd) are preferable because their efficiency is good. If they have hydrogenation activity, they can be in a metal form. Otherwise, they are supported on a carrier such as alumina, silica or silica-alumina, or they may be in the forms of transition metal compounds such as chlorides or acetates which are reducible under the hydrogen treatment condition.

The reaction temperatures in the method of the invention are preferably in the range of 20° C. to 170° C., and more preferably in the range of 40° C. to 150° C. When the temperature is lower than 20° C., the treatment time is unpractically long because of the low efficiency in dehalogenation. On the other hand, when the temperature is higher than 170° C., it is also undesirable because undesiratle nuclear hydrogenation of aromatic nuclei of substituted propionic acid is intense. The pressure in hydrogen treatment is not any substantial factor in the present invention. That is, the reaction can be done at any pressure at or above atmospheric pressure, which means that a suitable pressure can be selected according to the temperature of reaction so as to maintain the reaction system in a liquid phase. In practice, pressures up to 80 kg/cm$^2$ are preferable.

In the method of the present invention, the hydrogen treatment is carried out under a basic condition in the presence of liquid phase water. That is, the halogen produced by dehalogenation is rapidly neutralized by the basic substance and converted into inert halogenide, thereby preventing the produced halogen from the recombination of it with the dehalogenated product, the 2-(aryl substituted)propionic acid. In other words, conditions other than the basic condition are not desirable because contamination with impurities is invited. In this case, in order to cause the neutralization to proceed rapidly, the presence of liquid phase water is desirable so as to maintain the above basic substance in an aqueous solution.

As the basic substances for this purpose, there are exemplified by organic amines such as trimethylamine, triethylamine and tributylamine; alkali metal lower alcoholates such as sodium methoxide, potassium methoxide, sodium ethoxide and potassium ethoxide; as well as ammonia, inorganic alkali metal substances of alkali metal hydroxides such as sodium hydroxide and potassium hydroxide and alkali metal carbonates such as sodium carbonate, potassium carbonate, sodium hydrogencarbonate and potassium hydrogencarbonate. In practice, inorganic alkaline substances are preferable. The addition quantity of the basic substance may be the amount which is excess to neutralize the substituted propionic acid if it is produced in the form of free acid and the halogen produced by the dehalogenation and further to make the reaction system basic. When the substituted propionic acid is obtained in the form of a salt, the quantity of the basic substance is only on the level sufficient to neutralize the halogen produced by dehalogenation and to make the reaction system basic.

It is only necessary for water to exist in a liquid phase. The water miscible organic solvents of alcohols such as methanol, ethanol and ethylene glycol, and acetone, dioxane and tetrahydrofuran can coexist with water in a dissolved state.

The quantity of water is sufficient if it can dissolve the above basic substances and the 2-(aryl substituted)propionic acid.

The duration for the hydrogen treatment is not especially limited. The times in the range of 30 minutes to several tens of hours are generally sufficient in batchwise system.

The 2-(aryl substituted)propionic acid exists in the form of a salt after the reaction because the method of the present invention is carried out under a basic condition. Accordingly, in order to obtain a highly pure salt of 2-(aryl substituted)carboxylic acid, the catalyst is removed by an ordinary method such as filtration after the reaction which is followed by the removal of solvent by evaporation and crystallization in a known method. While, in the case that a highly pure free 2-(aryl substituted)propionic acid is obtained from the salt, the catalyst is removed by an ordinary method such as filtration after the reaction, the salt is changed into highly pure free 2-(aryl substituted)propionic acid and it is then precipitated. The quantity of the addition of acid is such that the pH of the reaction mixture in basic condition is made below 7. The precipitated free acid is then filtered to obtain highly pure 2-(aryl substituted)propionic acid.

The present invention will be described in more detail with reference to several examples.

EXAMPLE 1

The 2-(aryl substituted)propionic acids shown in the following Table 1 were synthesized by the conventional method. The results of the preparation are also shown in Table 1.

In the synthesis, halogenated by-products owing to the free halogen molecules or ions that are inherent to these processes, were inevitably formed. The contents of these halogenated by-products as converted to chlorine are also shown in Table 1.

TABLE 1

| Synthesis of 2-(aryl substituted)propionic acids | | |
|---|---|---|
| 2-(aryl substituted)-propionic acid | Chlorine Content (ppm) | Melting Point (°C.) |
| 2-phenylpropionic acid | 66 | 26–28 |
| 2-(p-isobutylphenyl)-propionic acid | 25 | 74–76 |
| 2-(m-benzoylphenyl)-propionic acid | 70 | 93–96 |
| 2-(m-phenoxyphenyl)-propionic acid | 90 | 172–175 (b.pt, 0.5 mmHg) |
| 2-(6-methoxynaphthyl)-propionic acid | 270 | 154–158 |

Each of the above 2-(aryl substituted)propionic acid (10 g) was added to 100 g of water. With stirring, 20% aqueous solution of sodium hydroxide was added slowly to dissolve completely the acid and the solution was made alkaline of pH 8 to 8.5. After that, it was fed into an autoclave equipped with a stirrer together with 0.5 g of palladium catalyst carried on activated carbon (catalyst content: 2.5 wt.%). The pressure in the autoclave was raised to 10 kg/cm$^2$ with hydrogen and allowed to react at 60° C. for 7 hours with stirring. After the reaction, the palladium catalyst was removed by filtration and the pH value of the filtrate was adjusted to 2 to 3 by slowly adding 35% hydrochloric acid. In this step, there appeared milky turbidity of substituted propionic acid of the reaction product in the filtrate. By adding each 25 ml of n-hexane, extraction was repeated four times. The n-hexane was removed under reduced pressure to obtain crystalline powder or liquid substance. With regard to these products of hydrogen treatment, the recovery rates and chlorine contents are shown in the following Table 2.

TABLE 2

Results of Hydrogen Treatment

| 2-(aryl substituted)-propionic acid | Recovery Rate (%) | Chlorine Content (ppm) |
| --- | --- | --- |
| 2-phenylpropionic acid | 94 | 7 |
| 2-(p-isobutylphenyl)-propionic acid | 96 | 8 |
| 2-(m-benzoylphenyl)-propionic acid | 96 | 9 |
| 2-(m-phenoxyphenyl)-propionic acid | 92 | 7 |
| 2-(6-methoxynaphthyl)-propionic acid | 96 | 7 |

EXAMPLE 2

Alumina was immersed into an aqueous solution of chloroplatinic acid and it was dried by removing water under reduced pressure. It was then treated in a flow of hydrogen at 450° C. for 3 hours to obtain a catalyst (catalyst content: 2.5%). Using this catalyst, 2-phenylpropionic acid, the same as the starting material in Example 1, was treated in the like manner as Example 1 except that the hydrogen treatment was done at a temperature of 90° C., pressure of 15 kg/cm² for 8 hours, thereby obtaining white crystals of 13 ppm in chlorine content with a recovery rate of 94%.

EXAMPLE 3

Asbestos was soaked with an aqueous solution of rhodium chloride and it was then reduced by immersing it into a mixed aqueous solution of formaldehyde and sodium hydroxide to obtain a catalyst (catalyst content: 2%). Using this catalyst, treatment was carried out in the like manner as Example 2, thereby obtaining white crystals of 14 ppm in chlorine content with a recovery rate of 92%.

COMPARATIVE EXAMPLE 1

In the like manner as Example 1, recrystallization of 2-phenylpropionic acid, the same as the starting material in Example 1, was carried out by using n-hexane. The results are shown in the following Table 3.

TABLE 3

Results of Recrystallization

| Recovery Rate (%) | Chlorine Content (ppm) |
| --- | --- |
| 26 | 16 |
| 54 | 23 |
| 77 | 44 |

As will be understood from the above results, in connection with 2-phenylpropionic acid containing halogenated by-products, the halogen cannot be eliminated effectively by the refining of simple recrystallization.

COMPARATIVE EXAMPLE 2

To 30 ml of n-hexane was dissolved 2.5 g of 2-(p-isobutylphenyl)propionic acid used in Example 1 as a starting material. It was fed into a 200 ml autoclave having a stirrer together with 0.13 g of palladium catalyst carried on activated carbon (catalyst content: 5 wt.%). Reaction was carried out at 60° C. for 4 hours under hydrogen pressure of 10 kg/cm². After the reaction, the palladium catalyst was removed by filtration and n-hexane was removed under reduced pressure to obtain 2-(p-isobutylphenyl)propionic acid of 73°–75° C. in melting point and 10 ppm in chlorine content with a recovery rate of 96%.

The chlorine content was reduced to 10 ppm by the hydrogenation, however, the melting point of the obtained product was lowered and the range of it was wide, which shows that the purity is low in the condition other than the basic condition.

EXAMPLE 4

Through a well known method, IPA was synthesized, which contained halogenated IPA (37 ppm as chlorine) derived from free halogen molecules and halogen ions inherent in the preparation method. Recrystallization was carried out by using n-hexane as a solvent.

In the recrystallization, 15 g of the above synthesized IPA was dissolved in 40 g of n-hexane by heating and it was left to become cool to separate out crystals. After cooling, the refined crystals were separated by filtration. n-Hexane in the filtrate was removed under reduced pressure and 4.5 g of light yellow solid containing concentrated impurities was recovered. It was confirmed that this light yellow solid contained mainly IPA by analytical procedures of NMR, IR, etc. The analytical results of chlorine content was 95 ppm and it was confirmed that the most part of chlorine content of the above synthesized IPA was concentrated into the filtrate.

The thus obtained yellow crystals (4 g) was dissolved into 45 g of 2% aqueous solution of sodium hydroxide and it was fed into a 200 ml autoclave equipped with a stirrer together with 0.2 g of palladium catalyst carried on activated carbon (catalyst content: 2 wt.%). The pressure in the autoclave was raised to 10 kg/cm² with hydrogen and allowed to react at 50° C. for 5 hours with stirring. After the reaction, the palladium catalyst was removed by filtration and the filtrate was acidified by slowly adding 7 g of 15% hydrochloric acid. In this step, there appeared milky turbidity of the precipitate of 2-(p-isobutylphenyl)propionic acid. By adding each 20 ml of n-hexane, extraction was repeated four times. The n-hexane was removed under reduced pressure to obtain white crystals (recovery rate: 93%).

Chlorine analysis was carried out with regard to this product to obtain a chlorine content of 4 ppm, by which it was confirmed that the reaction product could be refined to a highly pure level. In addition, it was confirmed that the IPA containing impurities could be recovered in a pure form with a quite high recovery rate.

EXAMPLE 5

Through a well known method, IPA containing halogenated by-product of 215 ppm converted as chlorine, was synthesized. Recrystallization was carried out by using a water/methanol mixed solvent (water/methanol: 22/78 by volume).

In the recrystallization, 25 g of the IPA was dissolved in 150 g of the mixed solvent by heating and it was left to become cool to separate out crystals. After cooling, the refined crystals were separated by filtration. The mixed solvent in the filtrate was removed under reduced pressure and 10.5 g of light yellow solid containing concentrated impurities was recovered. The analytical results of chlorine content was 450 ppm and it was confirmed that the most part of chlorine content was concentrated into the filtrate.

The thus obtained yellow solid was allowed to react with hydrogen in the like manner as Example 4 except the following conditions. Alumina was immersed into an aqueous solution of chloroplatinic acid and water content was removed by heating. It was then treated in a flow of hydrogen at 450° C. for 3 hours to obtain a catalyst carried on alumina (catalyst content: 5 wt.%). Using 0.2 g of this catalyst, the light yellow solid was allowed to react with hydrogen. After the reaction, white crystals of 75°–76° C. in melting point and 8 ppm in chlorine content was obtained in the like manner as Example 4 (recovery rate: 94%).

EXAMPLE 6

Asbestos was soaked with an aqueous solution of rhodium chloride and it was then reduced by immersing it into a mixed aqueous solution of formaldehyde and sodium hydroxide to obtain a catalyst carried on asbestos. Using this catalyst, treatment was carried out in the like manner as Example 5, thereby obtaining white crystals of 12 ppm in chlorine content (recovery rate: 94%).

COMPARATIVE EXAMPLE 3

In the like manner as the recrystallization procedure of Example 4, recrystallization of light yellow solid in Example 5 was carried out again. As a result, it was understood that the pure IPA could not be obtained effectively only by the repetition of recrystallization. The results of chlorine analysis are shown in the following Table 4.

TABLE 4

| Chlorine Content in Repeatedly Recrystallized IPA | |
|---|---|
| Recovery Rate (%) | Chlorine Content (ppm) |
| 76 | 340 |
| 54 | 170 |
| 34 | 97 |

COMPARATIVE EXAMPLE 4

To 30 ml of n-hexane was dissolved 2.5 g of the light yellow solid IPA of 450 ppm in chlorine content that was obtained in Example 5. It was fed into a 200 ml autoclave having a stirrer together with 0.2 g of palladium catalyst carried on activated carbon (catalyst content: 5 wt.%). Reaction was carried out at 60° C. for 9 hours under hydrogen pressure of 10 kg/cm$^2$. After the reaction, the palladium catalyst was removed by filtration and n-hexane was removed under reduced pressure to obtain refined IPA of 73°–75° C. in melting point and 52 ppm in chlorine content with a recovery rate of 97%.

The chlorine content was reduced to 52 ppm by the hydrogenation, however, the range of melting point of the obtained crystals was wide as compared with that of Example 5 and its temperature was low. This fact shows that the purity is low when the hydrogenation is done in a condition other than the basic condition.

What is claimed is:

1. A method for refining 2-(aryl substituted)propionic acid or its salt which is characterized in that 2-(aryl substituted)propionic acid or its salt containing halogenated by-product is brought into contact with hydrogen in a liquid phase containing water under a basic condition at temperatures in the range of 20° C. to 170° C. in the presence of a catalyst of transition metal of the group VIII in the periodic table, thereby dehalogenating said halogenated by-product and producing highly pure 2-(aryl substituted)propionic acid or its salt.

2. The method for refining 2-(aryl substituted)propionic acid or its salt in claim 1, wherein said catalyst of transition metal of the group VIII in the periodic table is at least one member selected from the group consisting of palladium, rhodium and platinum.

3. The method for refining 2-(aryl substituted)propionic acid or its salt in claim 1, wherein said 2-(aryl substituted)propionic acid is at least one member selected from the group consisting of 2-phenylpropionic acid, 2-(alkylphenyl)propionic acid, 2-(aryloxyphenyl)propionic acid, 2-(arylcarbonylphenyl)propionic acid, and 2-(methoxynaphthyl)propionic acid.

4. The method for refining 2-(aryl substituted)propionic acid or its salt in claim 1, wherein said 2-(aryl substituted)propionic acid is at least one member selected from the group consisting of 2-(p-isobutylphenyl)propionic acid, 2-(m-phenoxyphenyl)propionic acid, 2-(m-benzoylphenyl)propionic acid, and 2-(6-methoxynaphthyl)propionic acid.

5. The method for refining 2-(aryl substituted)propionic acid or its salt in claim 1, wherein said 2-(aryl substituted)propionic acid or its salt containing halogenated by-product is contained in the filtrate that is separated by the filtration of precipitated 2-(aryl substituted)propionic acid or its salt in the recrystallization step.

6. The method for refining 2-(aryl substituted)propionic acid or its salt in claim 1, wherein said halogen is chlorine.

7. The method for refining 2-(aryl substituted)propionic acid or its salt in any one of claims 1 to 6, wherein the salt of 2-(aryl substituted)propionic acid which is obtained by the contact with hydrogen, is recovered in a free acid form by acidifying below pH 7 with the addition of an acid.

8. The method for refining 2-(aryl substituted)propionic acid or its salt in any one of claims 1 to 6, wherein said basic condition is made up by using at least one member selected from the group consisting of amines, metal lower alcoholates and inorganic alkaline substances.

* * * * *